US005539132A

United States Patent [19]

Royer et al.

[11] Patent Number: 5,539,132

[45] Date of Patent: Jul. 23, 1996

[54] CERULENIN COMPOUNDS FOR FATTY ACID SYNTHESIS INHIBITION

[75] Inventors: Garfield P. Royer, Cashtown, Pa.; Craig A. Townsend, Baltimore, Md.

[73] Assignees: Johns Hopkins University; Chektec Corporation, both of Baltimore, Md.

[21] Appl. No.: 188,409

[22] Filed: Jan. 24, 1994

[51] Int. Cl.[6] ........................ C07D 303/38; C07D 303/46

[52] U.S. Cl. ........................ 549/545; 549/548; 549/354

[58] Field of Search ........................ 514/410; 549/354, 549/545

[56] References Cited

U.S. PATENT DOCUMENTS 3,897,428 7/1975 Omura et al. ........................ 544/176

OTHER PUBLICATIONS

Morisaki, N., et al, *Chem. Pharm. Bull.* 40(11) 2945–2953 (Nov. 1992) "Synthesis of Cerulenin and Its Analogs. I. Cerulenin and Its Analogs with Modified Side Chain".

Shimazawa, R., et al, *Chem. Pharm. Bull.* 40 (11) 2954–2957 "Synthesis of Cerulenin and Its Analogs. II. Synthesis and Biological Activity of dl–Carbacerulenin, a Carbocyclic analog of Cerulenin" (1992).

Morisaki, N., et al, *Eur. J. Biochem.* 211, 111–115 (1993) "Effect of side–chain structure on inhibition of yeast fatty––acid synthase by cerulenin analogues".

Omura, S., et al, *Antimicrobial Agents And Chemotherapy,* vol. 6, No. 2, Aug. 1974, pp. 207–215 "Relationship Between the Structures of Fatty Acid Amide Derivatives and Their Antimicrobial Activities."Jakubowski, A. A., et al, *J. Org. Chem.,* 1982 47, 1221–1228 "Total Syntheses of (±)–Cerulenin, (±)–Tetrahydrocerulenin, and Related Compounds."Boeckman, R. K., Jr., et al, *J. Amer. Chem. Soc.* 101:4, Feb. 14, 1979, 987–994 "A Total Synthesis of dl–Cerulenin."Corey, E. J., et al, *Tetrahedron Letters* No. 44, pp. 3847–3850, 1977 (Pergamon Press. Printed in Great Britain) "A Total Synthesis Of (35 )–Cerulenin."Yoda, H., et al, *Tetrahedron Letters,* vol. 32, No. 46, pp. 6771–6774, 1991 "A Novel Stereoselective Synthesis of (±)–Cerulenin and (±)–Tetrahydrocerulenin."Funabashi, H., et al, *J. Biochem.,* 105, 751–755 (1989) "Binding Site of Cerulenin in Fatty Acid Synthetase."D'Agnolo, G., et al, *Biochimica et Biophysica Acta,* 326 (1973) 155–166 "Inhibition of Fatty Acid Synthesis By The Antibiotic Cerulenin; Specific Inactivation of β–Ketoacyl–Acyl Carrier Protein Synthetase."

*Primary Examiner*—Alan L. Rotman
*Attorney, Agent, or Firm*—Nixon & Vanderhye

[57] ABSTRACT

Novel compounds for use in inhibiting fatty acid synthesis are disclosed. The compounds can be used for the treatment of tumors or microbial infections.

7 Claims, No Drawings

CERULENIN COMPOUNDS FOR FATTY ACID SYNTHESIS INHIBITION

This invention relates to novel compounds useful for inhibiting fatty acid synthesis. In particular, this invention contemplates administration of novel compounds to mammals having a tumor or microbial infection.

BACKGROUND OF THE INVENTION

Fatty Acid Metabolism

The fatty acid biosynthetic pathway in man is comprised of four major enzymes: acetyl-CoA carboxylase, the rate limiting enzyme which synthesizes malonyl-CoA; malic enzyme, which produces NADPH; citrate lyase, which synthesizes acetyl-CoA; and fatty acid synthase, which catalyzes NADPH-dependent synthesis of fatty acids from acetyl-CoA and malonyl-CoA. The final products of fatty acid synthase are free fatty acids which require separate enzymatic derivatization with coenzyme-A for incorporation into other products. In man, significant fatty acid synthesis may occur in two sites: the liver, where palmitic acid is the predominant product (Roncari, *Can. J. Biochem.*, 52:221–230, 1974); and lactating mammary gland where $C_{10}$–$C_{14}$ fatty acids predominate (Thompson, et al., *Pediatr. Res.*, 19: 139–143, 1985). Except for lactation, and cycling endometrium (Joyeux, et al., *J. Clin. Endocrinol. Metab.*, 70:1319–1324, 1990), the fatty acid biosynthetic pathway is of minor physiologic importance, since exogenous dietary fatty acid intake down-regulates the pathway in the liver and other organs (Weiss, et al., *Biol. Chem. Hoppe-Seyler,* 367:905–912, 1986).

In liver, acetyl-CoA carboxylase, malic enzyme and fatty acid synthase are induced in concert by thyroid hormone and insulin via transcriptional activation and repressed by glucagon (Goodridge, *Fed Proc.*, 45:2399–2405, 1986) and fatty acid ingestion (Blake, et al., *J. Nutr.*, 120:1727–1729, 1990). Tumor necrosis factor alpha (TNF) a cytokine with profound effects on lipogenesis, is either stimulatory or inhibitory depending on the cell type studied. TNF markedly inhibits lipogenesis in adipocytes by reduction in acetyl-CoA carboxylase and fatty acid synthase protein synthesis, but is markedly stimulatory in the liver by increasing the level of citrate, which is the primary allosteric activator of the rate limiting enzyme of fatty acid biosynthesis, acetyl-CoA-carboxylase.

In lactating breast, the other major site of fatty acid biosynthesis in humans, fatty acid synthesis is under control of prolactin, estrogen, and progesterone. During pregnancy, progesterone acts as a mitogen to promote breast development and concomitantly down-regulates prolactin receptors, preventing lipid and milk protein synthesis before delivery. After delivery, the fall in estrogen and progesterone levels allows up-regulation of prolactin receptors and subsequent increase in lipogenic enzymes and milk protein production by breast epithelial cells.

Regulation of fatty acid synthase expression in human breast cancer has been studied primarily as a model for progesterone-stimulated gene expression. In contrast to normal lactating breast where progesterone stimulates epithelial cell growth while retarding lipogenic enzyme synthesis, in progesterone receptor (PR) positive human breast carcinomas such as MCF-7, ZR-75-1, and T-47D, progesterone inhibits growth and induces fatty acid synthase production along with other lipogenic enzymes (Chambon, et al., *J. Steroid Biochem.*, 33:915–922 (1989). Progesterone presumably acts to up-regulate fatty acid synthase expression via the steroid hormone response element as is found in the rat fatty acid synthase promoter (Amy, et al., *Biochem. J.*, 271:675–686, 1989), leading to increased FAS mRNA transcription or, by other mechanisms, to increased message stability (Joyeux, et al., *Mol. Endrocinol.*, 4:681–686, 1989). Regarding PR-negative human breast cancer cells, a single study reports that fatty acid synthase accounts for about 25% of cytosolic protein in SKBR3 cells but no data regarding its biologic significance or regulation was available (Thompson, et al., *Biochim. Biophys. Acta,* 662:125–130, 1981).

With regard to cytokines and other lipogenic hormones, only scant data are available concerning human breast cancer. For example, TNF has been known to be markedly growth inhibitory to some breast cancer cultures. While TNF is mildly growth inhibitory to primary rat hepatocyte cultures ($ID_{50}$=5000 units/ml), some human breast cancer cells such as MCF-7 are extremely growth inhibited ($ID_{50}$=40 units/ml) (Chapekar, et al., *Exp. Cell. Res.*, 185:247–257, 1989). The effect of TNF on FAS expression or lipogenic activity in breast cancer cells, however, remains unknown. One study of fatty acid synthase expression in MCF-7 cells using Northern analysis, found that insulin and insulin growth factor-1 were only slightly stimulatory compared to 5–10 fold increases seen with progesterone, while $T_3$ had no effect (Chalbos, et al., *J. Steroid Biochem. Molec. Bid.*, 43:223–228, 1992). Overall, regulation of FAS in receptor positive breast cancer has been only cursorily examined, while receptor negative tumors have not been studied.

No association with poor clinical outcome was found for breast or for any other cancers in those few systems where fatty acid synthase expression was studied. In the only study purporting to associate FAS expression with prognosis, fatty acid synthase expression was studied by in situ hybridization in 27 breast cancers, finding an association between increased fatty acid synthase mRNA and a higher degree of morphologic differentiation, but without association with estrogen or progesterone receptor status (Chalbos, et al., *J. Natl. Cancer Inst.*, 82:602–606, 1990). It was deduced from these data that fatty acid synthase expression in breast carcinoma is associated with greater degree of morphologic differentiation and therefore presumably with less aggressive tumors. A second study of 87 cases by Northern blotting of fatty acid synthase mRNA found an association of fatty acid synthase expression and young age (premenopausal patients), but again no association with receptor status (Wysocki, et al., *Anticancer Res.*, 10:1549–1552, 1990). Neither study provided clinical follow-up of their patients; there were no data comparing FAS expression with either disease-free interval or patient survival. Without clinical outcome, no reliable conclusions can be drawn regarding FAS expression and tumor virulence.

These studies stand in contrast to a series of greater than 200 patients from several centers demonstrating a strong association between poor prognosis and expression of a protein of undetermined function (designated OA-519) through measurement of disease-free survival or overall survival (Kuhajda, *N. Engl. J. Med.*, 321:636–641, 1989; Shurbaji, et al., *Am. J. Clin. Pathol*, 96:238–242, 1991; Corrigan, et al., *Am. J. Clin. Pathol.*, 96:406, 1991; Cote, et al., *Lab. Invest.* ,66:13A, 1992; Ziegler, et al., *Am. J. Clin. Oncol.*, 14: 101–110, 1991).

Nor has fatty acid metabolism been a target of study in cancer therapeutics. Fujii, et al. (1986, *Japan J. Exp. Med.*, 56:99–106), used the fatty acid synthase inhibitor cerulenin in combination with exogenous antitumor antibodies to weaken the cell membrane in an attempt to potentiate complement-mediated cell membrane damage via the membrane attack complex. Cerulenin was known to be toxic to cells at high concentration, and Fujii, et al., taught that the cerulenin concentration should be kept low to maintain the selectivity conferred by the humoral immune component of complement-mediated cell lysis. Spielvogel, et al., U.S. Pat. No. 5,143,907, noted that a series of phosphite-borane compounds exhibited both antineoplastic activity and anti-inflammatory activity while lowering serum cholesterol and serum triglycerides. The phosphite-borane compounds are non-specific inhibitors that affect many cellular functions, and so they are not selectively effective against tumor cells. Spielvogel, et al. taught that the hypolipidemic effect on serum cholesterol and triglycerides was mediated through more than one mechanism, and the antineoplastic effect was not shown to be related to the hypolipidemic activity.

Cerulenin is a potent inhibitor of fatty acid biosynthesis at the level of the FAS complex (S. Omura, Bacteriological Reviews, September 1976, p. 681–697, Vol. 40 No. 3). The structure of cerulenin and the mechanism of action are shown below:

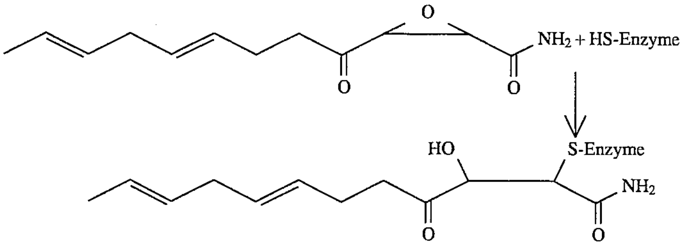

The alkylation of the critical enzyme thiol inactivates the Beta-ketoacyl-ACP synthetase component of the FAS multienzyme complex. Cerulenin may be viewed as having an enzyme binding moiety (the nine carbon diene) and a reactive group (the keto epoxy amide).

Cerulenin was originally isolated as a potential antifungal antibiotic from the culture broth of *Cephalosporium caerulens*. Structurally cerulenin has been characterized as 2R,3S-epoxy-4-oxo-7,10-trans,trans-dodecanoic acid amide. Its mechanism of action has been shown to be inhibition, through irreversible binding, of β-ketoacyl-ACP synthase, the condensing enzyme required for the biosynthesis of fatty acids. Cerulenin has been categorized as an antifungal, primarily against *Candida* and *Saccharomyces* sp. In addition, some in vitro activity has been shown against some bacteria, actinomycetes, and mycobacteria, although no activity was found against *Mycobacterium tuberculosis*. The activity of fatty acid synthesis inhibitors and cerulenin in particular has not been evaluated against protozoa such as *Toxoplasma gondii* or other infectious eucaryotic pathogens such as *Pneumocystis carinii, Giardia lamblia, Plasmodium sp., Trichomonas vaginalis, Cryptosporidium, Trypanosoma, Leishmania*, and *Schistosoma.*

Despite cerulenin's in vitro activity against some bacteria and fungi it has not been developed as a therapeutic agent. To date research on this compound has centered on it use as a research tool for investigating the role of fatty acids in the metabolism and physiology of a variety of organisms because of its activity as a fatty acid synthesis inhibitor.

SUMMARY OF THE INVENTION

It is an object of this invention to provide novel compounds and a method for treating carcinoma patients which will reduce the tumor burden of the patient.

It is another object of this invention to provide novel compounds and a method for treating virulent carcinomas.

The present invention provides a method of treating patients with carcinoma by inhibiting fatty acid synthesis by the cells of the carcinoma, such that growth of the cells is inhibited in a manner selectively cytotoxic or cytostatic to the cancer cells.

In a more particular embodiment, the invention provides a method of treating a host with a carcinoma by administering novel fatty acid synthase (FAS) inhibitors and/or inhibitors of other enzymes of the synthetic pathway for fatty acid as cytotoxic chemotherapeutic agents, thereby reducing tumor burden.

In a further embodiment, the present invention provides a method of ameliorating tumor burden in a host having tumor tissue which expresses a protein that exhibits fatty acid synthase activity, comprising administering a therapeutically effective amount of a novel fatty acid synthase inhibitor. Expression is determined directly in tumor tissues by detecting fatty acid synthase in tissue samples obtained from procedures such as biopsies, resections or needle aspirates, using assays such as immunohistochemistry, cytosol enzyme immunoassay or radioimmunoassay, or direct measurement of enzyme activity. Expression of fatty acid synthase by the tumor is indirectly measured by detecting fatty acid synthase in plasma or body fluid using assays such as enzyme immunoassay or radioimmunoassay.

In a further embodiment, the invention provides a method for treating a host with a carcinoma while protecting normal (non-neoplastic) tissues (such as liver, which may normally express fatty acid synthase activity) over a wide range from potential toxicity, by down-regulating the FAS enzyme activity of normal cells before and/or during administration of therapeutically effective amounts of novel FAS inhibitors. Down regulation may be accomplished by, for instance, reduction of caloric intake or other effective methods.

Particularly virulent carcinomas tend, among other things, to have cells that express OA-519, and this particular protein has been found to have fatty acid synthase activity which appears to be a required enzyme activity for the growth of carcinomas but not necessarily for normal cells. The compounds and methods of the subject invention are for treating carcinomas by administering novel inhibitors of fatty acid synthesis to reduce tumor burden in the patients. The methods of the invention are particularly advantageous because treatment with inhibitors such as FAS inhibitors is selective for cells expressing fatty acid synthase. FAS is an inducible enzyme that is not generally expressed by normal cells, and as a result, the tumor cells are preferentially affected by the inhibitors.

This invention also describes the use of novel inhibitors of fatty acid biosynthesis as a means to treat various opportunistic organisms known to express the fatty acid biosynthetic pathway. The drug concentrations required to inhibit growth of these infectious agents in vitro indicate a potential therapeutic index in man. Moreover, some of these infectious agents, such as *M. tuberculosis*, have fatty acid biosynthetic enzymes which are structurally similar, but not identical, to mammalian fatty acid synthase.

DETAILED DESCRIPTION OF THE INVENTION

I. FAS

The protein FAS (also referred to herein as OA-519) is highly correlated with the most virulent carcinomas. FAS exhibits fatty acid synthase activity. FAS purified from a human breast carcinoma cell line has peptide sequence homology with rat fatty acid synthase, and FAS also has functional characteristics of a fatty acid synthase. Fatty acid synthesis by FAS was demonstrated by incorporation of $^{14}C$ malonyl coenzyme A into fatty acids, subsequent esterification of the fatty acids, and analysis by reversed-phase thin layer chromatography. The specific activity of purified FAS was determined spectrophotometrically by following the oxidation of NADPH at 340 nm in the presence of acetyl coenzyme A and malonyl coenzyme A. In one determination, the specific activity of FAS was measured as 586 nanomoles NADPH oxidized/min/mg protein, which compares favorably with the value of 404 obtained for FAS from human liver.

Fatty acid synthase is a large protein found in the cytosol of cells from particular tissues, including liver and lactating mammary gland, but FAS is not expressed in most normal (non-malignant) adult tissues. Fatty acid synthase in higher organisms is a multifunctional enzyme which is well known to carry out the following seven enzymatic functions on a single molecule (Wakil, S. J., *Biochemistry,* 28:4523–4530, 1989):

acetyl transacylase
malonyl transacylase
beta-ketoacyl synthetase (condensing enzyme)
beta-hydroxyacyl dehydrase
enoyl reductase
thioesterase Breast cancer cells have been found to express fatty acid synthase, while most other rumor cells have not been tested for the presence or absence of this enzyme. Rochefort and co-workers have partially cloned FAS from breast cancer cells and found that FAS expression by breast cancer cell lines was correlated with responsiveness to progesterone (Chalbos, et al, *J. Biol. Chem,,* 262:9923–9926, 1987). Based on this evidence, they concluded that cells expressing FAS were from tumors that were less de-differentiated and therefore less virulent (Chalbos, et al, *J. Nat'l. Cancer Inst.,* 82:602–606, 1990).

Inhibitors of FAS inhibit growth of carcinoma cells, but have little effect on normal human fibroblasts. Indeed, fibroblasts, which have very low FAS activity, are resistant to FAS inhibitor concentrations that inhibit growth of more than 80% of breast carcinoma cells having high levels of FAS activity. Studies with multiple breast, prostate, lung, colon, and ovarian carcinoma cell lines, and normal fibroblasts confirm the correlation between FAS synthase activity and growth inhibition by FAS inhibitors. The relationship between drug sensitivity and FAS enzyme activity holds for all tumor cell types tested. Thus, inhibition of the fatty acid synthase enzyme, which is highly expressed in the most virulent carcinomas, can inhibit the growth of cells in these tumors.

II. Treatment Based on Inhibition of Fatty Acid Synthesis

The present invention provides a method for ameliorating tumor burden in a host whose tumor contains cells that are dependent on endogenously synthesized fatty acid (fatty acid synthesized within the cells). Such cells usually over-express a protein with FAS activity. Tumor burden may be reduced in such hosts by administering to the host one or more novel inhibitors that interfere with fatty acid synthesis or utilization. These inhibitors are cytotoxic to tumor cells which express FAS, and administration which results in reduction of fatty acid synthesis and utilization by the tissue and/or reduction of FAS activity in biological fluids of these hosts will reduce tumor burden. See the U.S. application entitled Chemotherapy for Cancer filed Jan. 24, 1994, hereby incorporated in its entirety.

The present invention also provides a method for inhibiting growth of microbial cells that are dependent on endogenously synthesized fatty acid (i.e., fatty acid synthesized within the cells) without inhibiting metabolic activity of the patient. Such microbial cells usually over-express a protein with FAS activity. Sepsis may be reduced in such patients by administering to the patient one or more novel inhibitors that interfere with fatty acid synthesis or utilization. These inhibitors are cytotoxic to microbial cells which express FAS, and administration which results in reduction of fatty acid synthesis and utilization by the microbial cells and/or reduction of FAS activity in biological fluids of these patients will reduce sepsis. See the U.S. application entitled Inhibitors of Fatty Acid Synthesis as Antimicrobial Agents filed Jan. 24, 1994, hereby incorporated in its entirety.

A. Selection of the Patient Population

The method of this invention can be used to treat hosts suffering from cancers which have an elevated level of fatty acid synthase. Characteristic carcinomas amenable to treatment include those of bladder, salivary gland, skin adnexa, bile duct, endocervix, ectocervix, and vagina, esophagus, nasopharynx and oropharynx, or those of germ cell origin, and mesothelioma. In particular, carcinomas or adenocarcinomas of the stomach, endometrium, kidney, liver and lung, as well as melanoma are treatable according to this invention. Breast, colon and rectum, prostate, and ovary, are especially suitable types of adenocarcinomas for the application of this therapy.

The method of this invention contemplates treatment of tumors having cells that express FAS or depend on endogenous fatty acid (synthesized within the cell). Endogenous fatty acid synthesis by such cells will preferably occur at a rate of incorporation greater than 10 fmoles of acetyl-CoA into acyl glyceride per 200,000 cells per minute. Preferred hosts are identified because they have tumors containing cells which express OA-519 or other enzymes of the fatty acid synthesis pathway, such as acetyl CoA carboxylase (ACC), at levels higher than the level found in the surrounding normal (e.g., non-neoplastic) tissue. Such cells are aggressive tumor cells and result in decreased survival, increased metastasis, increased rates of clinical recurrence and overall worsened prognosis.

Tumor cell sensitivity to fatty acid synthesis inhibitors usually varies continuously with FAS levels. Aggressive tumor cells expressing levels of FAS activity greater than 20 femtomoles malonyl CoA incorporated into fatty acid per 200,000 cells per minute may be expected to be sensitive to fatty acid synthase inhibitors. Since many tumor cells are extremely dependent on endogenous fatty acid synthesis, lower FAS activity levels need not exclude a specific tumor as a candidate for therapy with fatty acid synthase inhibitors.

Infectious diseases which are particularly susceptible to treatment by the method of this invention are diseases which cause lesions in externally accessible surfaces of the infected animal. Externally accessible surfaces include all surfaces that may be reached by non-invasive means (without cutting or puncturing the skin), including the skin surface itself, mucus membranes, such as those covering nasal, oral, gastrointestinal, or urogenital surfaces, and pulmonary surfaces, such as the alveolar sacs. Susceptible diseases include: (1) cutaneous mycoses or tineas, especially if caused by Microsporum, Trichophyton, Epidermophyton, or *Mucocutaneous candidiasis*; (2) mucotic keratitis, especially if caused by Aspergillus, Fusarium or Candida; (3) amoebic keratitis, especially if caused by Acanthamoeba; (4) gastrointestinal disease, especially if caused by *Giardia lamblia,* Entamoeba, Cryptosporidium, Microsporidium, or *Candida* (most commonly in immunocompromised animals); (5) urogenital infection, especially if caused by *Candida albicans* or *Trichomonas vaginalis*; and (6) pulmonary disease, especially if caused by *Mycobacterium tuberculosis,* Aspergillus, or *Pneumocystis carinii.* Infectious organisms that are susceptible to treatment with fatty acid synthesis inhibitors include *Mycobacterium tuberculosis*, especially multiply-drug resistant strains, and protozoa such as *Toxoplasma.*

The presence of FAS in cells of the carcinoma or in microbe cells can be detected by any suitable method, including activity assays or stains, immunoassays using anti-FAS antibodies, assays measuring FAS mRNA, and the like. Particularly advantageous are assays for the presence of OA-519, a protein which is immunologically cross-reactive with the gene product of the hpr gene (Maeda, *J. Biol. Chem.*, vol. 260, pp. 6698–6709, 1985) but not with haptoglobin 1 or 2. Such assays are taught in International Patent Publication WO 90/08324 or U.S. application Ser. No. 07/735,522, incorporated herein by reference. The most preferred assays are immunoassays for OA-519, either in tissue or in plasma.

Expression of FAS may be determined directly in tumor tissue samples obtained through procedures such as biopsies, resections or needle aspirates, using assays such as immunohistochemistry, cytosol enzyme immunoassay or radioimmunoassay, in situ hybridization of nucleic acid probes with mRNA targets having FAS sequences, or direct measurement of enzyme activity. Expression of fatty acid synthase by the tumor may be indirectly measured in biological fluid samples obtained from patients, such as blood, urine, serum, lymph, saliva, semen, ascites, or especially plasma, using any suitable assays. Preferred assays for FAS in biological fluid include enzyme immunoassay or radioimmunoassay.

Cells which depend on endogenously synthesized fatty acids may also be identified by detection of other enzymes of the fatty acid synthesis pathway at levels higher than those found in non-neoplastic tissue surrounding the rumor (normal tissue). In particular, treatment of cells having unexpectedly high levels of acetyl CoA carboxylase is contemplated by the present invention. The presence of these enzymes may be detected by assay methods analogous to those described for FAS.

Cells that require endogenously synthesized fatty acid are widespread among carcinomas, particularly the most virulent carcinomas. While it is preferred that the presence of FAS be determined prior to treatment, the skilled clinician will recognize that such determination is not always necessary. Treatment of a carcinoma patient with an inhibitor of fatty acid synthesis, particularly a FAS inhibitor, which results in reduction of tumor burden demonstrates the presence of FAS in the tumor. Where a carcinoma patient can be successfully treated by the method of this invention, independent determination of FAS may be unnecessary. Such empirical treatment of carcinomas of the type usually found to express FAS is also within the contemplation of this invention.

Fatty acid synthesis inhibitors of the invention are also useful in conjunction with other chemotherapeutic agents. Since no presently prescribed cancer chemotherapeutic agents are specifically active against the fatty acid synthase pathway, FAS inhibitors will complement existing anticancer drags, particularly antimetabolic drugs that target other anabolic or catabolic pathways.

Fatty acid synthesis inhibitors of the invention are also useful in conjunction with other antimicrobial agents. Since no presently prescribed antimicrobial agents are specifically active against the fatty acid synthase pathway, the novel FAS inhibitors will complement existing antibiotic drugs, particularly antimetabolic drugs that target other anabolic or catabolic pathways.

FAS expression and the growth inhibitory effect of inhibitors of the fatty acid synthetic pathway are independent of the cell cycle. Therefore, inhibitors of fatty acid synthesis may be expected to be particularly effective in combination with chemotherapeutic agents that target rapidly cycling cells. Alternatively, the fatty acid synthesis inhibitors of the invention may be administered to supplement a chemotherapeutic regime based on antineoplastic agents known to be effective against the particular tumor type being treated. In particular, use of fatty acid synthesis inhibitors to prevent the growth of a small proportion of undetected but highly virulent cells in conjunction with a therapeutic program using other agents is within the contemplation of this invention.

On the other hand, it is not contemplated that fatty acid synthesis inhibitors will be useful in combination with agents which produce complement-mediated cell damage via the membrane attack complex, whether initiated by antibody or by the alternative pathway for complement activation (Bhakdi, et al. (1983), "Membrane Damage by Complement," *Biochim. Biophys. Acta,* 737:343:372). Therefore, this invention is not directed to the use of fatty acid synthesis inhibitors in the presence of exogenously supplied agents which activate the complement-dependent membrane attack complex.

B. Inhibition of the Fatty Acid Synthetic Pathway

Carcinoma cells or microbial cells which are dependent on their own endogenously synthesized fatty acid will express FAS. This is shown both by the fact that FAS inhibitors are growth inhibitory and by the fact that exogenously added fatty acids can protect normal cells but not these carcinoma cells from FAS inhibitors. Therefore, preventing synthesis of fatty acids by the cell may be used to treat carcinoma or microbial infection.

Fatty acids are synthesized by fatty acid synthase (FAS) using the substrates acetyl CoA, malonyl CoA and NADPH. Thus, the fatty acid synthesis pathway is usually considered to involve four enzymes—FAS and the three enzymes which produce its substrates: acetyl CoA carboxylase (ACC), malic enzyme and citrate lyase. Other enzymes which can feed substrates into the pathway, such as the enzymes which produce NADPH via the hexose monophosphate shunt, may also affect the rate of fatty acid synthesis, and thus be important in cells that depend on endogenously synthesized fatty acid. Inhibition of the expression or the activity of any of these enzymes will affect growth of carcinoma cells or microbial cells that are dependent on endogenously synthesized fatty acid.

The product of FAS is a free $C_{12}$–$C_{16}$ fatty acid, usually palmitate. Palmitic acid must be further processed to fulfill the requirements of the cells for various lipid components. As used herein, the term "lipid biosynthesis" refers to any one or a combination of steps that occur in the synthesis of fatty acids or subsequent processing of fatty acids to make cellular components containing fatty acids. The first step in this down-stream processing is activation of the fatty acid by coupling it to coenzyme A, which is catalyzed by an enzyme, acyl CoA synthetase.

Inhibition of key steps in down-stream processing or utilization of fatty acids may be expected to inhibit cell function, whether the cell depends on endogenous fatty acid or utilizes fatty acid supplied from outside the cell, and so inhibitors of these down-stream steps may not be sufficiently selective for tumor cells or microbial cells that depend on endogenous fatty acid. However, administration of a fatty acid synthesis inhibitor to such cells makes them more sensitive to inhibition by inhibitors of down-stream fatty acid processing and/or utilization. Because of this synergy, administration of a fatty acid synthesis inhibitor in combination with one or more inhibitors of down-stream steps in lipid biosynthesis and/or utilization will selectively affect tumor cells that depend on endogenously synthesized fatty acid. Preferred combinations include an inhibitor of acyl CoA synthetase combined with an inhibitor of FAS or ACC.

C. Inhibitors of Fatty Acid Synthesis

When it has been determined that a host has a tumor which expresses FAS, or in infected with cells of an organism which expresses FAS, or if FAS has been found in a biological fluid from a host, the host may be treated according to the method of this invention by administering a novel fatty acid synthesis inhibitor to the host.

Any compound that inhibits fatty acid synthesis can be used to inhibit tumor cell or microbial cell growth, but of course, compounds administered to the host must not be equally toxic to both malignant and normal (non-malignant) cells. Preferred inhibitors for use in the method of this invention are those with high therapeutic indices (therapeutic index is the ratio of the concentration which affects normal cells to the concentration which affects tumor cells). Inhibitors with high therapeutic index are identified by comparing the effect of the inhibitor on two cell lines, one non-malignant line, such as a normal fibroblast line, and one carcinoma line which has been shown to express high levels of FAS.

In particular, therapeutic index is determined by comparing growth inhibition of animal cells such as human cell lines exhibiting a low level of fatty acid synthesis activity, preferably less than about 10 fmole acetyl-CoA incorporation into acyl glyceride per minute per 200,000 cells, to growth inhibition of human cancer cells exhibiting a high level of fatty acid synthetic activity, preferably greater than about 20 fmole acetyl-CoA incorporation per 200,000 cells per minute, more preferably at least about 80 fmole acetyl-CoA incorporation into acyl glyceride per 200,000 cells per minute. Cells with the preferred level of fatty acid synthesis activity are easily obtained by the skilled worker. Preferably, the growth inhibition assays are performed in the presence of exogenous fatty acid added to the cell culture medium, for example, 0.5 mM oleic acid complexed to BSA.

Inhibitors are characterized by the concentration required to inhibit cell growth by 50% ($IC_{50}$ or $ID_{50}$). FAS inhibitors with high therapeutic index will, for example, be growth inhibitory to the carcinoma cells at a lower concentration (as measured by $IC_{50}$) than the $IC_{50}$ for the normal cells. Inhibitors whose effects on these two cell types show greater differences are more preferred. Preferred inhibitors of fatty acid synthesis will have $IC_{50}$ for cells with high fatty acid synthetic activity that is at least ½ log lower, more preferably at least 1 log lower, than the inhibitor's $IC_{50}$ determined for cells with low activity.

Lipid synthesis consists of multiple enzymatic steps. The data demonstrate that inhibition of lipid biosynthesis at two or more steps can create synergistic effects, lowering both the required concentration and potential toxicity of any single agent.

When tumors are treated by administration of a synergistic combination of at least one inhibitor of fatty acid synthesis and at least one inhibitor of either the enzymes which supply substrates to the fatty acid synthesis pathway or the enzymes that catalyze downstream processing and/or utilization of fatty acids, the therapeutic index will be sensitive to the concentrations of the component inhibitors of the combination. Optimization of the concentrations of the individual components by comparison of the effects of particular mixtures on normal and OA-519-expressing cells is a routine matter for the skilled artisan. The dose of individual components needed to achieve the therapeutic effect can then be determined by standard pharmaceutical methods, taking into account the pharmacology of the individual components.

The inhibitor of fatty acid synthesis, or the synergistic combination of inhibitors will be administered at a level (based on dose and duration of therapy) below the level that would kill the host mammal being treated. Preferably, administration will be at a level that will not irreversibly injure vital organs, or will not lead to a permanent reduction in liver function, kidney function, cardiopulmonary function, gastrointestinal function, genitourinary function, integumentary function, musculoskeletal function, or neurologic function. On the other hand, administration of inhibitors at a level that kills some cells which will subsequently be regenerated (e.g., endometrial cells) is not necessarily excluded.

Acetyl CoA carboxylase and the condensing enzyme of the FAS complex are candidates for inhibition. Fatty acid synthesis is reduced or stopped by inhibitors of these enzymes. The result would be deprivation of membrane lipids, which causes cell death. Normal cells, however, would survive as they are able to import circulating lipid. Acetyl CoA carboxylase is the focal point for control of lipid biosynthesis. The condensing enzyme of the FAS complex is well characterized in terms of structure and function; the active center contains a critical cysteine thiol, which is the target of antilipidemic reagents, such as cerulenin.

A wide variety of compounds have been shown to inhibit fatty acid synthase (FAS). FAS inhibitors can be identified by testing the ability of a compound to inhibit fatty acid synthase activity using purified enzyme. Fatty acid synthase activity can be measured spectrophotometrically based on the oxidation of NADPH, or radioactively by measuring the incorporation of radiolabeled acetyl- or malonyl-CoA. (Dils, et al, *Methods Enzymol,* 35:74–83). Several FAS inhibitors are disclosed in U.S. Ser. No. 08/096,908 and its CIP filed Jan. 24, 1994, both of which are hereby incorporated by reference. Included are inhibitors of fatty acid synthase, citrate lyase, CoA carboxylase, and malic enzyme.

Preferred inhibitors of the condensing enzyme include a wide range of chemical compounds, including alkylating agents, oxididents, and reagents capable of undergoing disulphide interchange. The binding pocket of the enzyme prefers long chain, E, E, dienes such as:

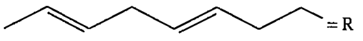

In principal, a reagent containing the sidechain diene shown above and a group which exhibits reactivity with thiolate anions could be a good inhibitor of the condensing enzyme. Cerulenin (2S) (3R) 2,3-epoxy-4-oxo-7,10 dodecadienoyl amide is an example:

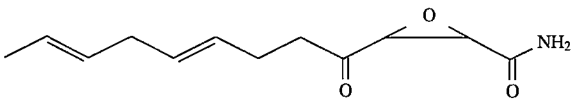

Cerulenin, a specific and non-competitive inhibitor of fatty acid synthase, was studied in tumor cells as a representative inhibitor of fatty acid synthesis. Cerulenin covalently binds to a thiol group in the active site of the condensing enzyme of fatty acid synthase, inactivating this key enzymatic step (Funabashi, et al., *J. Biochem.*, 105:751–755, 1989). The condensing enzyme reaction, which catalyzes the condensation of malonyl-CoA with an acetyl group or with the nascent fatty acid chain, generating $CO_2$, is the most specific reaction of the synthase and is not shared by other enzymes. While cerulenin has been noted to possess other activities, these either occur in microorganisms which may not be relevant models of human cells (e.g. inhibition of cholesterol synthesis in fungi, Omura (1976), *Bacteriol. Rev.*, 40:681–697; or diminished RNA synthesis in viruses, Perez, et al. (1991), *FEBS*, 280: 129–133), occur at a substantially higher drug concentrations (inhibition of viral HIV protease at 5 mg/ml, Moelling, et al. (1990), *FEBS*, 261:373–377) or may be the direct result of the inhibition of endogenous fatty acid synthesis (inhibition of antigen processing in B lymphocytes and macrophages, Falo, et al. (1987), *J. Immunol.*, 139:3918–3923). Recent data suggests that cerulenin does not specifically inhibit myristoylation of proteins (Simon, et al., *J. Biol. Chem.*, 267:3922–3931, 1992).

TOFA (an inhibitor of acetyl CoA carboxylase) also demonstrated an anti-proliferative effect on a panel of cell lines with varying levels of FAS enzyme activity and fatty acid biosynthesis. TOFA can be used in combination with a novel inhibitor of the subject invention.

As can be seen in U.S. Ser. No. 08/096,908 and its CIP filed Jan. 24, 1994, cerulenin as well as inhibitors of other enzymes of fatty acid synthesis potently inhibit the growth of mammary, colon, and prostatic carcinoma lines. Furthermore, the potency of growth inhibition was proportional to the relative levels of fatty acid biosynthesis exhibited by these cultured cells. Cerulenin acts by creating a state of fatty acid starvation leading to cell death, which is proportional to the level of endogenous fatty acid synthesis.

Novel Compounds of the Invention

Three groups of novel chemical compounds are described herein:

Group A- Cerulenin (CE) analogs
- Class I- Modified reactive group
- Class II- Modified sidechain
- Class III- Modified reactive group and sidechain Group B- Geranyl (GE) analogs Group C- Dodecenoic Acid (DA) analogs Member compounds in each group show utility as inhibitors of therapeutically relevant enzymes, including, but not limited to, those of lipid biosynthesis/modification, mycocerosic acid synthetase, and enzymes of sterol biosynthesis.

GROUP A

CE Analogs Class I

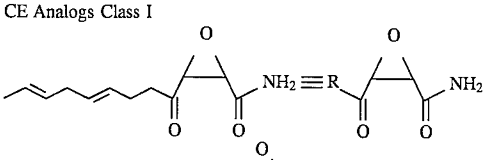

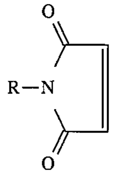

1

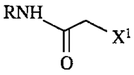

2

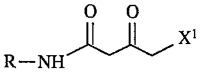

3

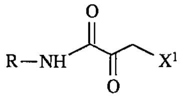

4

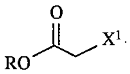

5

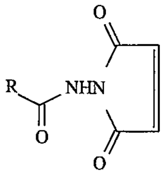

6

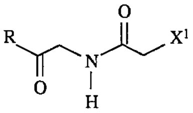

7

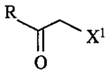

8

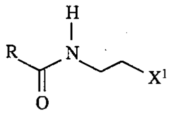

9

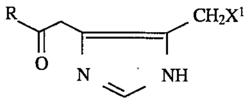

10

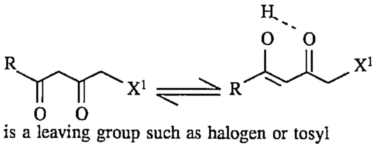

11

Where $X^1$ is a leaving group such as halogen or tosyl

Class II

-continued

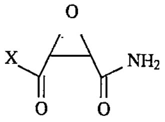

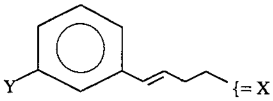

Where Y = R (H, akyl, alkenyl, alkynyl, cyclo-) halogen, OR, SR, $NR^1$, $R^2$

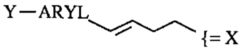 Y = as above

ARYL = pyridine, pyrrole, furan, thiophene, imidazole, triazole

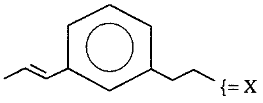

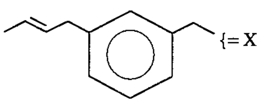

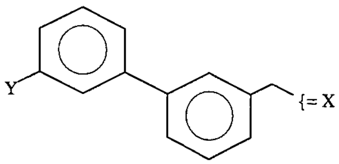 Y = as above

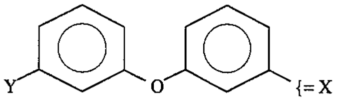 Y = as above

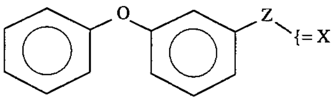 Where Z = $CH_2$, O, S, NH

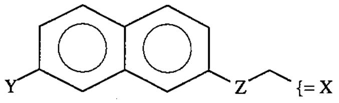 Y = as above
Z = as above

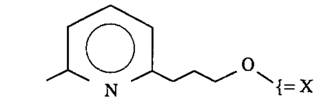

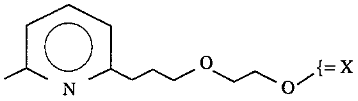

Class III combinations of electrophilic groupings as in Class I with side chain residues as in Class II - and other structural types as:

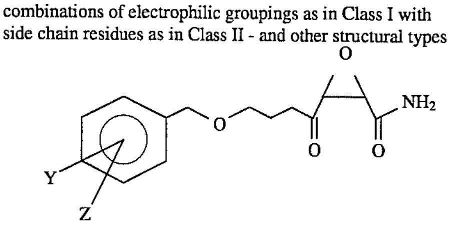

Where Y and Z = Subst. as in Y above

-continued

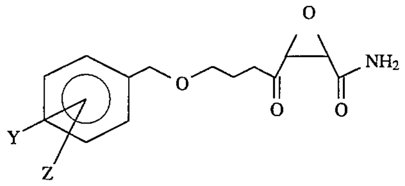

Y and Z as above

GROUP B

GE Analogs

A. 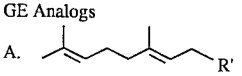

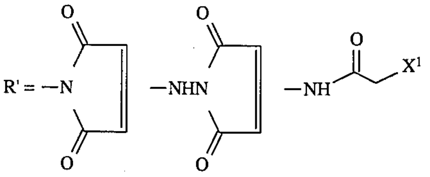

1 2 3

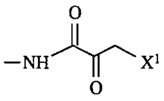

4

B. 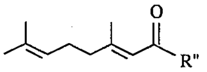

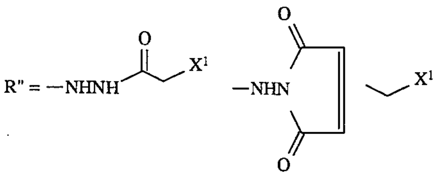

1 2 3

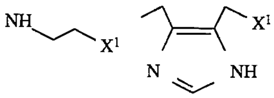

4 5

C. 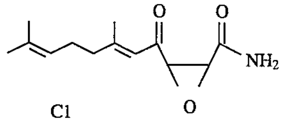

C1

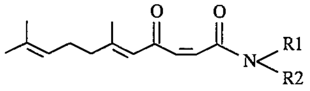

C2

$R_1$ and $R_2$ can be identical or different $R_1$ and $R_2$ can be hydrogen, alkyl, alkenyl, cdoalkyl, aralkyl D. 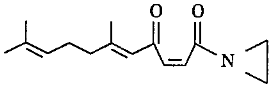

1

-continued

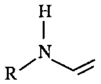

2

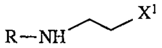

3

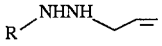

4

$R-CH_2X^1$

5

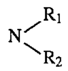

6

{$R_1$ AND $R_2$ as described earlier}

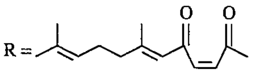

Group C

DA Analogs

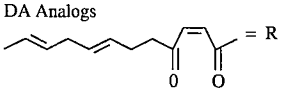

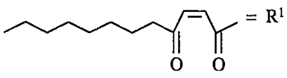

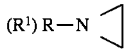

1

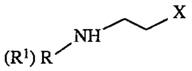

2

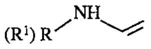

3

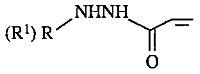

4

$(R^1) R-CH_2Cl$

5

In addition to acetyl CoA carboxylase and FAS, other target enzymes include citrate lyase and malic enzyme. These enzymes provide acetate and NADPH for lipid biosynthesis via FAS. The respective reactions are as follows:

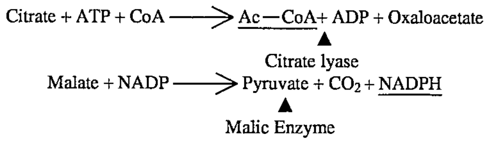

Therapeutic compounds could also be based on these inhibitors as the deprivation of acetyl CoA or NADH would also stop the lipid synthesis.

Of the enzymes in the fatty acid synthetic pathway, FAS is the preferred target for inhibition because it acts only within the pathway to fatty acids, while the other three enzymes are implicated in other cellular functions. Therefore, inhibition of one of the other three enzymes is more likely to affect normal cells. However, where an inhibitor for one of these enzymes can be shown to have a high therapeutic index as described above, the inhibitor may be used therapeutically according to this invention. The skilled clinician will be able to select a method of administration and to administer inhibitors of any enzyme in the synthetic pathway for fatty acids to treat carcinoma patients in need of such treatment, based on the teaching below.

Palmitate is the major product of the fatty acid synthetase pathway. The elongation and oxidation of palmitate may be critical for production of necessary membrane lipids. For that purpose, the elongation and oxidation steps and any other processing steps for fatty acids would be likely molecular targets for therapeutics. To be incorporated into lipids, both endogenously synthesized fatty acids and exogenous dietary fatty acids must first be activated by acyl-CoA synthetase. Long-chain fatty acyl-CoA is an essential metabolite for animal cells, and so acyl-CoA synthetase is a preferred target.

Tomoda and colleagues (Tomoda et..al., *Biochim. Biophys. Act* 921:595–598 1987; Omura el. al., *J. Antibiotics* 39:1211–1218 1986) describe Triacsin C (sometimes termed WS-1228A), a naturally occurring acyl-CoA synthetase inhibitor, which is a product of Streptomyces sp. SK-1894. The chemical structure of Triacsin C is 1-hydroxy-3-(E, E, E-2',4',7' -undecatrienylidine) triazene. Triacsin C causes 50% inhibition of rat liver acyl-CoA synthetase at 8.7 μM; a related compound, Triacsin A, inhibits acyl CoA-synthetase by a mechanism which is competitive for long-chain fatty acids. Inhibition of acyl-CoA synthetase is toxic to animal cells. Tomoda et. al. (Tomoda el. al., *J. Biol. Chem.* 266:4214–4219, 1991) teaches that Triacsin C causes growth inhibition in Raji cells at 1.0 μM, and have also been shown to inhibit growth of Vero and Hela cells. Tomoda el. al. further teaches that acyl-CoA synthetase is essential in animal cells and that inhibition of the enzyme has lethal effects. Triacsin C can be used in combination with the novel inhibitors of the subject invention.

Lipid synthesis consists of multiple enzymatic steps. The data demonstrate that inhibition of lipid biosynthesis at two or more steps can create synergistic effects, lowering both the required concentration and the potential toxicity of any single agent. Since acyl-CoA synthetase is a ubiquitous enzyme apparently required by all cells for their continued well being, its inhibitors are potentially too toxic to be used effectively as a single anti-cancer agent. In contrast, when acyl-CoA synthetase inhibitors are paired with a cerulenin derivative, a specific fatty acid synthase inhibitor, synergistic effects are obtained, rendering each drug more effective.

D. Administration of Inhibitors of Fatty Acid Synthesis

Inhibitors of fatty acid synthesis are preferably formulated in pharmaceutical compositions containing the inhibitor and a pharmaceutically acceptable carrier. The pharmaceutical composition may contain other components so long as the other components do not reduce the effectiveness of the synthesis inhibitor so much that the therapy is negated. Pharmaceutically acceptable carriers are well known, and one skilled in the pharmaceutical art can easily select carriers suitable for particular routes of administration (*Remington's Pharmaceutical Sciences*, Mack Publishing Co., Easton, Pa., 1985).

The pharmaceutical compositions containing any of the inhibitors of this invention may be administered by parenteral (subcutaneously, intramuscularly, intravenously, intraperitoneally, intrapleurally, intravesicularly or intrathecally, topical, oral, rectal, or nasal route, as necessitated by choice of drug, tumor type, and tumor location.

Dose and duration of therapy will depend on a variety of factors, including the therapeutic index of the drugs, tumor type, patient age, patient weight, and tolerance of toxicity. Dose will generally be chosen to achieve serum concentrations from about 0.1 μg/ml to about 100 μg/ml. Preferably, initial dose levels will be selected based on their ability to achieve ambient concentrations shown to be effective in in-vitro models, such as that used to determine therapeutic index, and in-vivo models and in clinical trials, up to maximum tolerated levels. Standard procedure in oncology requires that chemotherapy be tailored to the individual patient and the circulatory concentration of the chemotherapeutic agent be monitored regularly. The dose of a particular drug and duration of therapy for a particular patient can be determined by the skilled clinician using standard pharmacological approaches in view of the above factors. The response to treatment may be monitored by analysis of blood or body fluid levels of fatty acid synthase, measurement of FAS activity or OA-519 levels in tumor tissue or monitoring tumor burden in the patient. The skilled clinician will adjust the dose and duration of therapy based on the response to treatment revealed by these measurements.

In an advantageous mode, the inhibitor of fatty acid synthesis is formulated in a pharmaceutical composition and applied to an externally accessible surface of the animal. Diseases which cause lesions in externally accessible surfaces may be treated by non-invasive administration of an inhibitor of fatty acid synthesis. Non-invasive administration includes (1) topical application to the skin in a formulation, such as an ointment or cream, which will retain the inhibitor in a localized area; (2) oral administration; (3) nasal administration as an aerosol; (4) intravaginal application of the inhibitor formulated in a suppository, cream or foam; (5) rectal administration via suppository, irrigation or other suitable means; (6) bladder irrigation; and (7) administration of aerosolized formulation of the inhibitor to the lung. Aerosolization may be accomplished by well known means, such as the means described in International Patent Publication WO 93/12756, pages 30–32, incorporated herein by reference.

An advantageous strategy is to administer these compounds locally or topically in gels, ointments, solutions, impregnated bandages, liposomes, or biodegradable microcapsules. Compositions or dosage forms for topical application may include solutions, lotions, ointments, creams, gels, suppositories, sprays, aerosols, suspensions, dusting powder, impregnated bandages and dressings, liposomes, biodegradable polymers, and artificial skin. Typical pharmaceutical carriers which make up the foregoing compositions include alginates, carboxymethylcellulose, methylcellulose, agarose, pectins, gelatins, collagen, vegetable oils, mineral oils, stearic acid, stearyl alcohol, petrolatum, polyethylene glycol, polysorbate, polylactate, polyglycolate, polyanhydrides, phospholipids, polyvinylpyrrolidone, and the like.

A particularly preferred formulation for fatty acid synthesis inhibitors is in liposomes. Liposomes containing fatty acid synthesis inhibitors according to this invention may be prepared by any of the methods known in the art for preparation of liposomes containing small molecule inclusions. Liposomes that are particularly suited for aerosol application to the lungs are described in International Patent Publication WO 93/12756, pages 25–29, incorporated herein by reference.

The compositions described above may be combined or used together or in coordination with another antineoplastic, antibiotic, antifungal or antiviral substance.

E. Selective Chemotherapeutic Method

In a preferred embodiment, the method of this invention also protects normal cells of patients treated with fatty acid synthesis inhibitors. To protect normal tissues such as liver (which normally may express wide ranges of fatty acid synthase activity) from potential toxicity, the level of FAS enzyme and/or fatty acid synthetic activity may be down-regulated before and/or during therapy. Down regulation may be accomplished by supplying essential fatty acids in the diet, by reduction of caloric intake or by other effective methods, such as administration of glucagon.

Because FAS is an inducible enzyme in normal tissues, reduction in caloric intake will result in lower expression of FAS by normal cells. The most virulent tumor cells express FAS (OA-519) constitutively. In a patient with limited caloric intake, FAS expression is limited to tumor cells, and the cytotoxic effect of FAS inhibitors will be similarly limited. Down-regulation of FAS expression is usually coupled to fatty acid synthesis inhibitor therapy by reducing caloric intake of the patient before and during administration of the inhibitor.

Another suitable method of reducing FAS expression is exogenous administration of fatty acids, preferably, essential fatty acids. These fatty acids may be formulated in any way that results in the down-regulating FAS expression of normal cells. This could be by including them in the diet of the patient or by formulating them in the same pharmaceutical composition as the fatty acid synthesis inhibitor, or any other suitable method.

Diets suitable for reducing FAS expression in normal tissue are easily within the skill of the ordinary clinician. Any method of reducing FAS expression by normal cells is within the contemplation of the method of this invention, as long as the FAS level in normal cells is reduced during the time that the fatty acid synthesis inhibitor is present in the patient at levels that would be cytotoxic to tumor cells.

EXAMPLES

The following Examples are provided for purposes of illustration only. They are not intended to limit the invention described above, which is only limited by the appended claims.

EXAMPLE 1

The synthesis of cerulenin-like molecules draws in part from existing methods for this FAS inhibitor. These routes include: R. K. Boeckman, Jr. et al *J. Am. Chem. Soc.* 1979, 101, 987; E. J. Corey and D. R. Williams *Tetrahedron Lett.* 1977, 3847; A. A. Jakubowski et al. *J. Org. Chem* 1982, 47, 1221; K. Mikami et al., *Chem. Lett.* 1981, 1721; T. Ohta et al. *Heterocycles* 1986, 24, 1137; H. Yoda et al. *Tetrahedron Lett.* 1991, 32, 6771. More recently side chain variations on the structure of cerulenin have been described (N. Morisaki et al. *Chem. Pharm, Bull.* 1992, 40, 2945), and the carbocyclic analogue of cerulenin has been prepared as well (R. Shimazawa et al. *Chem. Pharm. Bull.* 1992, 40, 2954).

SYNTHETIC SCHEME I

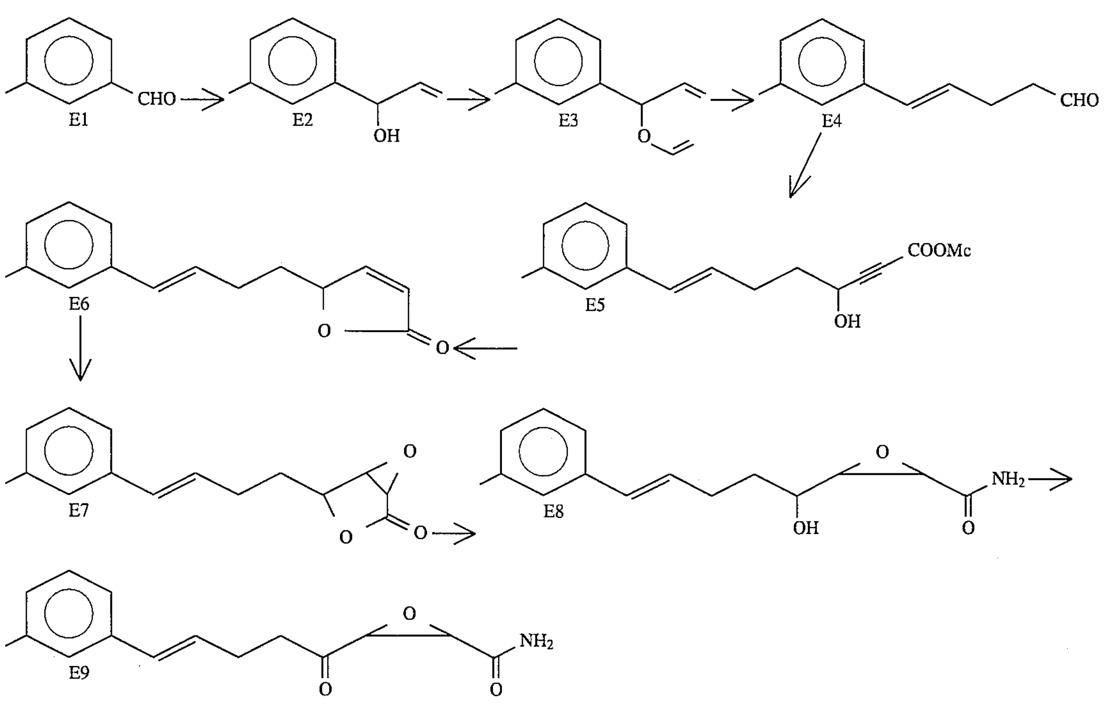

Vinyl alcohol E2: To 5 g of m-tolualdehyde in 70 mL of anhydrous ether at 0° C. was added vinyl magnesium bromide (41.6 mL of a 1 molar solution in tetrahydrofuran) over 45 min. After stirring for 5 h at 0° C. and 5 h at room temperature, the reaction was quenched with ammonium chloride solution and extracted with ether. The organic phase was dried over anhydrous magnesium sulfate and evaporated to yield a pale yellow oil used directly in the next step.
IR (neat): 3356, 3019, 2919, 1641, 1607 and 1487 $cm^{-1}$.
$^1$H-NMR ($CDCl_3$): d 2.25 (s, 3H), 5–5.28 (m, 3H), 5.93 (m, 1H), 7.12 (m, 4H).

Aldehyde E4: To 5.75 g of the vinyl alcohol E2 was added 70 ml of freshly distilled ethyl vinyl ether and 12.4 g of mercuric acetate. The mixture was heated to reflux, acetic acid added (1.2 g) and stirred for 3 h at room temperature. The reaction solution was partitioned between petroleum ether and 5% aqueous potassium hydroxide. The organic layer was washed with brine and dried over anhydrous sodium carbonate. The solvents were evaporated under reduced pressure to obtain the vinyl ether E3 (5.75 g, IR (ncat): 1635, 1611 $cm^{-1}$) as a light yellow oil. The product was homogeneous by thin layer chromatography and subjected to Claisen rearrangement without further purification.

The vinyl ether E3 was heated under nitrogen at 130°–150° C. for 5 h. The product was purified by column chromatography on silica gel (hexane:ethyl acetate 97.5:2.5) to yield the homogeneous aldehyde E4 as a colorless oil (4.75 g. 88%).
IR (neat): 2719, 1724, 1603, 1583, 1487 $cm^{-1}$.
$^1$H-NMR ($CDCl_3$): d 2.24 (s, 3H), 2.45 (d x t, J=6.0, 1.3 Hz, 2H), 2.49 (m, 2H), 6.08 (d x d x d x d, J=6.8, 12.7 15.7 Hz, 1H), 6.28 (d, J=15.7 Hz, 1H), 7–7.2 (m, 4H), 9.71 (t, J=1.3 Hz, 1H).
Exact Mass: calculated for $C_{12}H_{14}O$: 174.1045, found: 174.1048.

Acetylenic ester E5: Methyl propiolate (0.75 mL, 8.4 mmol) was added to 1.1 equiv. of lithium diisopropylamide cooled to −78° C. in 15 mL of dry tetrahydrofuran. After 30 min, 0.9 equiv. of aldehyde E4 was added in 3 mL of tetrahydrofuran and stirred for 3 h. Acetic acid was added (2 mL) and the reaction mixture was allowed to warm to room temperature over 3 h. The reaction was worked up with aqueous ammonium chloride and extracted with ether and the ether layer was washed with aqueous sodium bicarbonate, brine and dried over anhydrous magnesium sulfate. Removal of the solvent and chromatography on silica gel (hexane: ethyl acetate 90:10) gave E5 as an oil (1.5 g, 76%).
IR (neat): 3400, 2950, 2235, 1715, 1602, 1487, 1255 $cm^{-1}$.
$^1$H-NMR ($CDCl_3$): 1.94 (m, 2H), 2.25 (s, 3H), 3.75 (s, 3H), 4.52 (t, j=6.8 Hz, 1H), 6.2 (d x d x d, J=6.8, 12.7, 15.7 Hz, 1H), 6.40 (d, H=15.7 Hz, 1H), 7–7.2 (m, 4H).
Exact Mass: calculated for $C_{16}H_{18}O_3$: 258.1256, found 258.1256.

Butenolide E6: The hydroxy ester E5 (110 mg. 0.426 mmol) was hydrogenated in methanol (5 mL) and dry pyridine (0.4 mL) using Lindlar catalyst (5% Pd/$CaCO_3$, 30 mg). After the theoretical amount of hydrogen had been consumed, the mixture was diluted with ether and filtered through Celite to remove the catalyst. The organic solution was washed with 5% aqueous HCl, saturated aqueous sodium hicarbonate and dried over anhydrous magnesium sulfate. The volume was reduced to 25 mL and a catalytic amount of p-toluenesulfonic acid was added to carry out the lactonization. After stirring for 7 h at room temperature, the solution was washed with dilute aqueous sodium bicarbonate and dried as above. The solvents were removed under vacuum and chromatography on silica gel (hexanes:ethyl acetate 78:22) gave the butenolide E6 as a colorless oil (61 mg, 63%).
IR (neat): 3022, 2921, 1755, 1690, 1600 1445 $cm^{-1}$.
$^1$H-NMR ($CDCl_3$): d 1.77–1.95 (m, 2H), 2.32 (s, 3H), 2.36 (m, 2H), 5.06 (m, 1H), 6–6.22 (m, 2H), 6.39 (d, J=15.7 Hz, 1H), 7–7.22 (m, 4H), 7.48 (d, J=1.4 Hz, 1H).

Epoxylactone E7: To a solution of the butenolide E6 (50 mg, 0.219 mmol) in pyridine (2.5 mL) was added sodium hypochlorite (0.15 mL, 5% chlorine, diluted 1:1 with water). After stirring 2.5 h at 0° C., the mixture was allowed to come to room temperature and methylene chloride (15 mL) and water (5 mL) were added. The mixture was treated with 5% aqueous sodium bicarbonate (10 mL) and the aqueous solution was washed with ether and then acidified to pH 1 (0.5N HCl). The solution was then thoroughly extracted with ethyl acetate, dried over anhydrous magnesium sulfate. After removal of the solvents, the crude product was heated at 70° C. for 3 h to ensure complete closure of the epoxylactone. After chromatography on silica gel (hexanes:ethyl acetate 80:20), the product E7 was obtained as a glassy solid (28 mg, 52%).

IR (neat): 3023, 2922, 1783, 1603, 1583, 1587 $cm^{-1}$.

$^{1}$H-NMR ($CDCl_3$): d 1.91 (m, 2H), 2.44 (s, 3H), 2.48 (m, 2H), 3.87 (d, J=2.4 Hz, 1H). 4.08 (d, J=2.4 Hz, 1H), 4.74 (d x d, J=5.6, 7.5 Hz, 1H), 6.25 (d x d x d, J=6.9, 13.9, 15.7 Hz, 1H), 6.50 (d, J=15.7 Hz, 1H), 7.1–7.3 (m, 4H).

Exact Mass: calculated for $C_{15}H_{16}O_3$: 244.1099, found: 244.1102.

Hydroxyamide E8: The epoxylactone E7 (73 mg, 0.299 mmol) in methanol was treated with concentrated aqueous ammonium hydroxide (0.05 mL, excess). After stirring 1 h, the solution was diluted with methylene chloride (10 mL) and washed with 0.5N HCl. The solution was dried over anhydrous sodium sulfate, the solvents removed under vacuum to yield the product E8 as a white solid, which was recrystallized from ethyl acetate/hexanes (63 mg, 80%, mp 104°–106° C.).

IR (film): 3364, 1681, 1603 $cm^{-1}$.

$^{1}$H-NMR ($CDCl_3$): d 1.8 (m, 2H), 2.24 (s, 3H), 2.3 (m, 2H) 3.19 (m, 1H), 3.53 (d, J=5.6 Hz, 1H), 3.55 (m, 1H), 3.78 (br s, 1H), 6.2–6.5 (M, 4H), 7–7.35 (m, 4H).

Ketoamide E9: The hydroxamide E8 (72 mg, 0.275 mmol) was dissolved in methylene chloride (10 mL) and treated with 1 g of pyridinium chlorochromatic. After stirring for 2.5 h at room temperature, the reaction mixture was diluted with 35 mL of ether and the mixture was filtered through a plug of Celite. The crude product E9 was purified by flash chromatography on silica gel (hexanes:ethyl acetate 1:1) to yield the ketoamide E9 at a white solid (46 mg, 64%).

IR (film): 3335, 2923, 1713, 1684, 1594 $cm^{-1}$.

$^{1}$H-NMR ($CDCl_3$): d 2.33 (s, 3H), 2.3–2.4 (m, 2H), 2.74 (m, 2H), 3.74 (d, J=5.3 Hz, 1H), 3.88 (d, J=5.2, 1H), 5.47 (br s, 2H), 6.07 (d x d x d, J=6.8, 13.9, 15.7 Hz, 1H), 6.35 (d, J=15.7, 1H).

Exact Mass: calculated for $C_{15}H_{17}NO_3$: 259.1208, found: 259.1212

EXAMPLE 2

SYNTHETIC SCHEME II

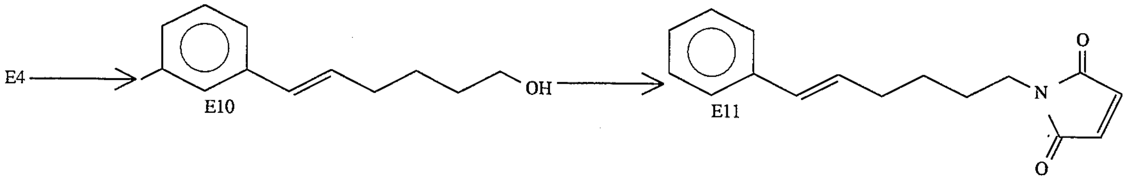
E4
E10
E11

Alcohol E10: Aldehyde E4 (1.5 g, 8.62 mmol) in methanol (50 mL) was treated with sodium borohydride (650 mg, 17.1 mmol) at room temperature. After stirring for 10 h, the volume was reduced to ca. 10 mL and 25 mL of aqueous ammonium chloride was added. The mixture was acidified to pH 1 with 0.5N HCl and extracted three times with ether. The organic extracts were dried over anhydrous magnesium sulfate, evaporated and the residue purified by flash chromatography to yield the desired alcohol E10 as a glass solid (1.45 g, 95%).

IR (neat): 3220, 2938, 1604 $cm^{-1}$.

$^{1}$H-NMR ($CDCl_3$): d 1.77 (m, 2H), 2.27 (s, 3H), 2.30 (m, 2H), 3.70 (t, J=6.3 Hz, 2H), 6.22 (d x d x d, J=6.8, 13.9, 15.7 Hz, 1H), 6.37 (d, J=15.7 Hz, 1H), 7–7.2 (m, 4H).

Maleimide E11: To a solution of alcohol E10 (840 mg, 4.77 mmol) in 20 mL of dry tetrahydrofuran was added diethyl azodicarboxylate (0.825 mL, 5.25 mmol) followed by maleimide (500 mg, 5.25 mmol) and triphenyl phosphine (1.37 g, 5.25 mmol). After stirring the solution at room temperature for 15 h, evaporation of the solvents afforded a yellow solid, which was filtrated with ether:hexanes 1:1 (300 mL) and the filtrate was evaporated under reduced pressure. The residue was purified by column chromatography on silica gel (hexanes:ethyl acetate 80:20) to yield the substituted maleimide E11 as a glassy solid (300 mg, 54% based on recovered E10).

IR (neat): 3660, 3098, 2939, 1704, 1603, 1584 $cm^{-1}$.

$^{1}$H-NMR ($CDCl_3$): d 1.75 (m, 2H), 2.20 (m, 2H), 2.30 (s, 3H), 3.55 (t, J=6.3 Hz, 2H) 6.17 (d x d x d, J=6.8, 13.9, 15.7 Hz, 1H), 6.38 (d, J=15.7 Hz, 1H), 6.62 (s, 2H), 7–7.2 (m, 4H).

Exact Mass: calculated for $C_{16}H_{17}NO_2$: 255.1259, found: 255.1262.

EXAMPLE 3

SYNTHETIC SCHEME III

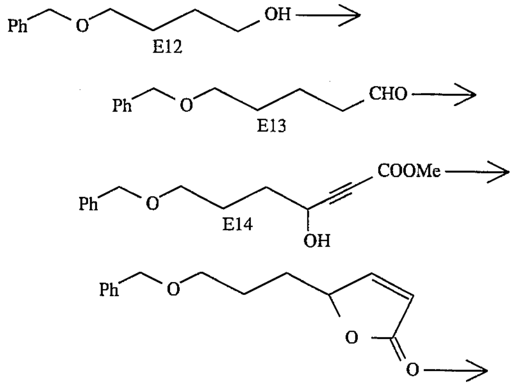
E12
E13
E14

-continued

SYNTHETIC SCHEME III

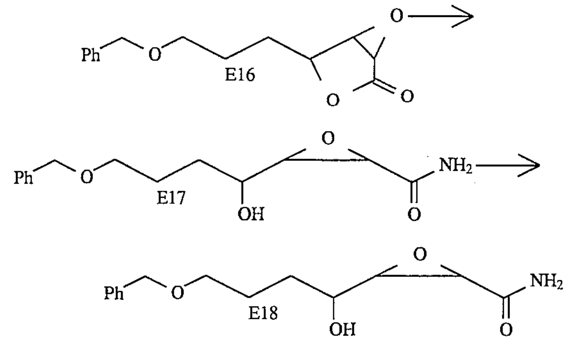

E16

E17

E18

Aldehyde E13: Chromium trioxide (3.79 g, 37.9 mmol) in methylene chloride (50 mL) was treated carefully with pyridine (6 g, 37.8 mmol) at 0° C. After stirring at 0° C. for 1 h, alcohol E12 (2.4 g, 13.3 mmol) was added in 10 mL of methylene chloride and stirring was continued overnight. The solvents were evaporated, the residue taken up in ethyl acetate and washed with 1N NCl, aqueous sodium bicarbonate solution and distilled water. The solution was dried over anhydrous magnesium sulfate, the solvent removed in vacuo and the residue purified by column chromatography (hexanes:ethyl acetate 90:10) to yield the aldehyde E13 as a colorless oil (1.7 g, 72%).

IR (neat): 2930, 1720, 1719, 1595, 1448, 1096 $cm^{-1}$.

$^1$H-NMR ($CDCl_3$): d 1.90 (m, 2H), 2.58 (d x t, J=1.5, 7.0 Hz, 2H), 3.48 (t, J=6.0 Hz, 2H), 4.48 (s, 2H) 7.31 (m, 5H), 9.77 (t, J=1.5 Hz, 1H).

Acetylenic ester E14: Aldehyde E13 (1.5 g, 8.42 mmol) was treated with methyl propiolate as above in Example 1 to give E14 after purification by chromatography on silica gel (hexanes:ethyl acetate 85:15) as a colorless oil (1.42 g, 65%).

IR (neat): 3398, 2953, 2235, 1717, 1453, 1435, 1255, 1096 $cm^{-1}$.

$^1$H-NMR ($CDCl_3$): d 1.88 (m, 4H), 3.51 (m, 2H), 3.77 (s, 3H), 4.54 (m, 3H), 7.31 (m, 5H).

Butenolide E15: The acetylenic ester E14 (854 mg, 3.25 mmol) was reduced and cyclized to the butenolide E15 as above in Example 1 to give 0.70 g (93%) as a colorless oil after chromatography on silica gel (hexanes:ethyl acetate 80:20).

IR (neat): 2936, 1755, 1659, 1600, 1495, 1362, 1163, 1102, 1017 $cm^{-1}$.

$^1$H-NMR ($CDCl_3$): d 1.5–1.7 (m, 4H), 3.41 (m, 2H), 4.57 (s, 2H), 5.05 (m, 1H), 6.09 (d, x d, J=2.0, 5.5 Hz, 1H), 7.30 (m, 5H), 7.44 (d, J=5.7 Hz, 1H).

Epoxylactone E16: The butenolide E15 (50 mg, 0.21 mmol) was epoxidized as in Example 1 to afford, after chromatography on silica gel (hexanes:ethyl acetate 85.15), the epoxylactone E16 as a glassy solid (31 mg, 60%).

IR (neat): 2926, 1784, 1453, 1180, 1099, 1025 $cm^{-1}$.

$^1$H-NMR ($CDCl_3$): d 1.76 (m, 4H), 3.50 (m, 2H), 3.76 (d, J=2.4 Hz, 1H), 3.96 (d, J=2.4 Hz, 1H), 4.50 (s, 2H), 4.58 (m, 1H), 7.32 (m, 5H).

Hydroxyamide E17: The epoxylactone E16 (20 mg, 0.08 mmol) in methanol was treated with concentrated aqueous ammonia (0.04 mL, excess) at 0° C. After 1 h, aqueous workup as in Example 1 furnished the hydroxyamide as a glassy solid (19 mg, 89%).

IR (neat): 3347, 2927, 1679, 1601, 1453 $cm^{-1}$.

$^1$-NMR ($CDCl_3$): d 1.75 (m, 4H), 3.08 (d x d, J=1.7, 4.6 Hz, 1H), 3.47 (m, 4H), 4.49 (s, 2H), 6.22 br d, $J_{app}$=8.4 Hz, 2H), 7.30 (m, 5H).

Ketoamide E18: Oxidation of hydroxyamide E17 ( 19 mg, 0.07 mmol) using chromium trioxide-pyridine complex (130 mg) as in Example 1 afforded the ketoamide E18 as a glass solid (13.5 mg, 72%).

IR (neat): 2928, 1717, 1684, 1455 $cm^{-1}$.

$^1$H-NMR ($CDCl_3$): d 1.81 (m, 2H), 2.67 (m, 2H), 3.44 (t, J=5.7 Hz, 2H) 3.71 (br d, 1H), 3.87 (br d, 1H), 4.49 (s, 2H), 6.4 (br s, 2H), 7.3 (m, 5H).

EXAMPLE 4

FAS Enzymatic assay for Testing Compound Activity

Methods:

Preparation of crude cell extracts: The potential of compounds to inhibit FAS enzymatic activity was determined using a crude cell extract of a cancer cell line or *Saccharomyces cerevisiae*. The breast cancer cell line ZR-75-1 was grown to confluence in RPMI with 10$FBS. The cells were harvested by scraping, washed once with cold phosphate buffered saline pH 7.5 and stored at –80° C. Extracts were prepared by thawing the cells in the presence of 4 vol. of 25 mM potassium phosphate pH 7.5, 1 mM EDTA, 1 mM DTT, 0.4% digitonin, 0.7 μg/ml pepstatin, 2 μg/ml aprotinin and 0.5 μg/ml leupeptin. Cells were homogenized with a Dounce type homogenizer for 20 strokes. Extracts were cleared by two sequential centrifugations at 30,000 xg, for 30 min each. The extract was dialyzed against 125 mM potassium phosphate pH 6.6, 1 mM EDTA, 1 mM DTT using a 100,000 molecular weight cut off membrane. The extract stored at 4° C. with 3 mM sodium azide. Yeast extracts were prepared from freeze-dried yeast. Yeast were reconstituted in 5 vol/g 100 mM potassium phosphate pH 6.5. Cells were harvested by centrifugation at 3,000 xg for 10 min. Cells were washed with 5 vol 100 mM potassium phosphate pH 6.5 and suspended in 2 vol. 125 mM potassium phosphate pH 6.6, 1 mM EDTA, 1 mM DTT, 0.7 μg/ml pepstatin, 2 μg/ml aprotinin and 0.5 μg/ml leupeptin. Sterile 0.5 mm glass beads were added (½ vol) and the mixture vortex vigorously for four 30 s intervals with 30 s rests on ice between mixes. Extracts were cleared by centrifugation and dialyzed as described above.

Testing of compound activity: Compounds were tested for their ability to inhibit FAS enzymatic activity by incubating the compounds with the crude cell extracts and measuring residual FAS activity. The compounds were mixed with a crude cell extract to the desired concentration and the mixture incubated at 10°–25° C. for 30 min. Residual FAS activity was measured as described below. The concentration of compound giving 50% maximal activity defined the $IC_{50}$ which was calculated from a 4-parameter equation of the dose-response curves.

Enzymatic assay conditions: The FAS enzyme activity was measured by monitoring the oxidation of NADPH spectrophotometrically (Dils, R. and E. M. Carey, 1975, Fatty acid synthase from rabbit mammary gland. Methods in Enzymol. 35:74–83). A 50 μl portion of an extract or extract-compound mixture was mixed with 50 μl 250 mM potassium phosphate pH 6.6, 40 μM acetyl-CoA, 200 μM malonyl-CoA, 1 mM NADPH and 2 mM DTT. The initial rate of NADPH oxidation at 25° C. was measured by monitoring the decrease in absorbance at 340 nm.

The results are shown in TABLE 1.

TABLE 1

$IC_{50}$ VALUES FOR INHIBITORS OF FAS ACTIVITY

| COMPOUND | STRUCTURE | $IC_{50}$ (μM) Cancer | Yeast |
|---|---|---|---|
| CTC002 Cerulenin | 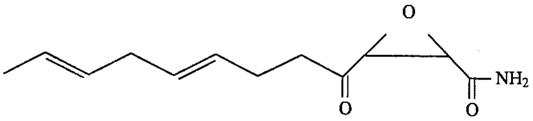 | 8.6 | 0.4 |
| CTC003 | 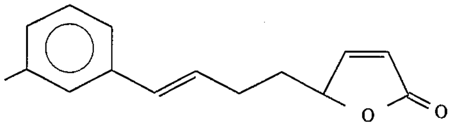 | >100 | N.T. |
| CTC004 | 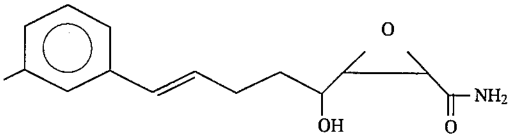 | >100 | N.T. |
| CTC005 | 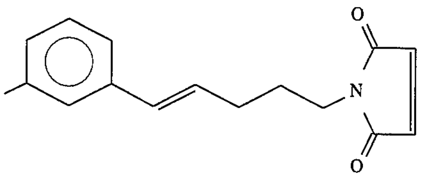 | >78 | N.T. |
| CTC006 (cyclic. cer.) | 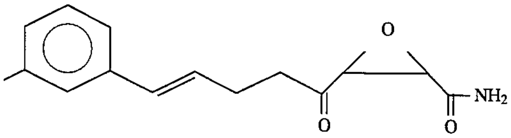 | 10.4 | 82 |
| CTC013 | 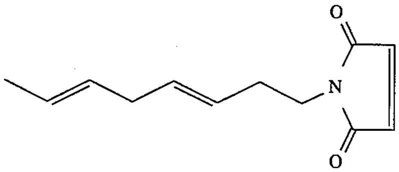 | >97 | N.T. |
| CTC014 | 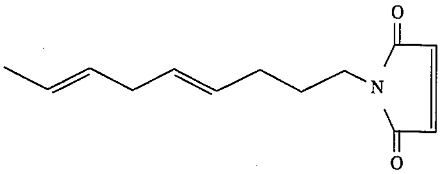 | >92 | N.T. |

N.T. - not tested

EXAMPLE 5

Growth inhibition asssay for testing compounds

Methods:

Cells were seeded at $5\times10^3$ per well into 96-well plates and incubated for 3 days in RPMI, 10% FBS at 37° C. in a 5% $CO_2$:95% air atmosphere. Medium was removed and replaced with media plus compound. Compound doses were 10 serial dilutions from 200 μg/ml to 0.39 μg/ml. Cells were returned to the incubator for 3 additional days. The medium was removed and plates were washed twice with phosphate buffered saline. Wells were filled with 100 μl of 0.2% crystal violet in 2% ethanol for 10 min. Stain was removed from the wells and the plates were washed 3 times with distilled $H_2O$. After at least 4 h of drying wells were filled with 100 μl of 1% SDS and plates were shaken to disolve any dye crystals. Absorbance at 560 nm minus 650 nm in each well was measured using a Molecular Devices plate reader. $IC_{50}$ values were calculated from 4-parameter curve-fits of the dose-response curves.

The results are shown in TABLE 2.

TABLE 2

IC$_{50}$ VALUES FOR INHIBITORS OF FAS IN GROWTH INHIBITION ASSAY

| COMPOUND | STRUCTURE | IC$_{50}$ SKBr 3 Cells µM | IC$_{50}$ HS 27 Cells µM |
|---|---|---|---|
| CTC002 Cerulenin | 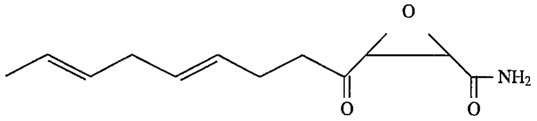 | 20 | 20 |
| CTC003 | 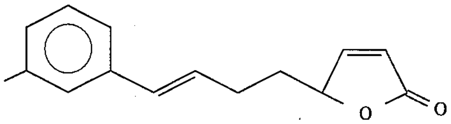 | >50 | >50 |
| CTC004 | 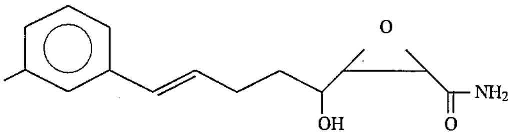 | >50 | >50 |
| CTC005 | 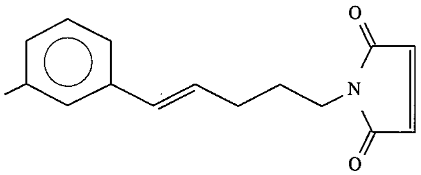 | >50 | >50 |
| CTC006 (Cyclic. cer.) | 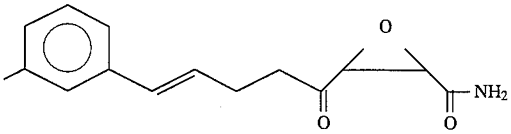 | 21 | 32 |
| CTC013 | 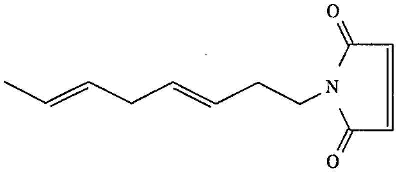 | 63 | 63 |
| CTC014 | 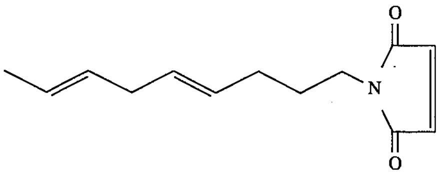 | >50 | >50 |

EXAMPLE 6

Description and Operation: Determination of the activity of the cerulenin derivative CTC 006 (phenyl cerulenin) against *M. tuberculosis* was performed utilizing a commercially available radiometric system which is based on the same principle that is utilized in conventional antibiotic susceptibility testing of *M. tuberculosis*. The significant difference between methods is that a liquid medium is used and rather than counting colonies after approximately 3 weeks of incubation, the growth is monitored through measurement of metabolism of $^{14}$C-labeled palmitic acid to $^{14}CO_4$ radiometrically with the results being available in 3 to 5 days. Drug susceptibility or resistance is determined by the modified version of the conventional proportion method. The critical proportion for resistance is taken as 1% for all antituberculosis drugs. Resistance is determined through comparison of the growth rate in control vials containing a 1% inoculum and broth vials containing the specific test drug. This method has been found comparable to the conventional proportional method or the resistance ratio method. Similarly accuracy and reproducibility of this method have yielded excellent results.

Materials and Methods:

Organisms

Mycobacteria: A control organism *M. tuberculosis* H37RV was used throughout the studies. Due to the relatively slow growth rate of *M. tuberculosis* H37RV, a *Candida albicans* strain known to be susceptible to cerulenin was used to control antibiotic concentration as well as *M. tuberculosis* H37RV. The remaining isolates of *M. tuberculosis* were clinical isolates from this institution or referred here as part of a cooperate susceptibility study on strains of obtained from patients seen in Haiti.

Susceptibility Test Method:

Mycobacteria: Susceptibility testing was performed using a commercially available Middlebrook 7H12 broth media containing $^{14}C$-labeled palmitate (12B Bactec bottles) as an indicator substrate. Growth in this system is determined through measurement of $^{14}CO_2$ generation from metabolism of the $^{14}C$-labeled palmitate. A 1 mg/ml initial stock solution of cerulenin was prepared and diluted to the following concentrations (μg/ml): 1000, 500, 250, 125, 62.5. A 0.1 ml of the stock concentrations were then added to individual 4.0 ml Bactec bottles resulting in the following final concentrations (μg/ml): 25, 12.5, 6.25, 3.0, 1.5. For each strain tested 0.1 ml of organism was added to each bottle at each concentration tested, a direct control (bottle containing diluent, DMSO, but no antibiotic, and a 1:100 organism dilution which is also added to broth bottle not containing antibiotic. All broth bottles were incubated at 35° C. and read daily for Growth Index (GI proportional to quantity of $^{14}CO_2$ generated) readings. Results were recorded until the GI of the 1:100 control reached 30. At this time, the minimum inhibitory concentration of the isolate wasdetermined. Control organisms for each susceptibility run included *Candida albicans* (cerulenin MIC<1.5 μg/ml). A 0.5 McFarland suspension of *C. albicans* is prepared and 0.1 ml of this suspension was added to each concentration of CTC 006 in the 12B Bactec bottles.

The minimum inhibitory concentration of each isolate was determined using the following criteria. Once the growth index (GI) of the 1:100 control bottle had reached a value of 30 the change (Δ) in growth index for a one day period was calculated as well as the growth index change (Δ) at each concentration tested during the same 24 hour period. The MIC was defined as the lowest cerulenin concentration that yielded a growth index change less than that of the 1:100 control bottle.

Results:

Mycobacteria: CTC 006, in this susceptibility test system, does have inhibitory activity against both susceptible and multiply drug resistant *M. tuberculosis* with minimum inhibitory concentrations ranging from <1.5 μg/ml to 6.25 μg/ml. Compound CTC 006 had an MIC of 25 μg/ml.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

We claim:

1. A compound having the formula:

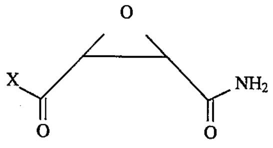

where X=

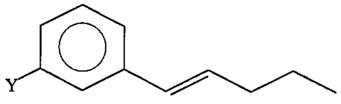

and where Y=R (H or methyl), or halogen.

2. A compound having the formula:

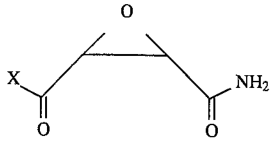

where X=

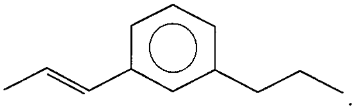

.

3. A compound having the formula:

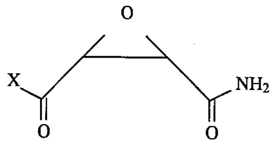

where X=

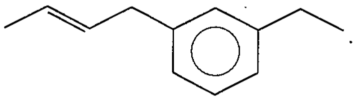

.

4. A compound having the formula:

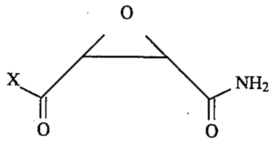

where X=

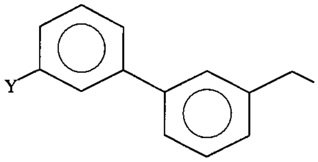

where Y=H or halogen.

5. A compound having the formula:
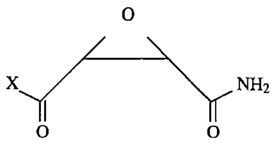
where X=
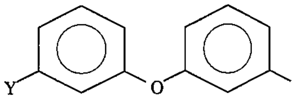
where Y=H or halogen.
6. A compound having the formula:
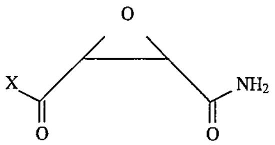
where X=
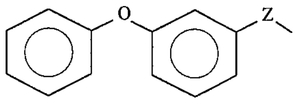
where Z=$CH_2$, O, S, or NH.
7. compound having the formula:
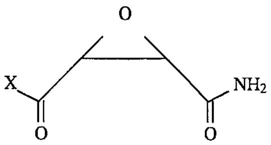
where X=
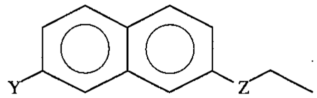
where Y=H or halogen, and where Z=$CH_2$, O, S, or NH.
* * * * *